United States Patent
Zanaty et al.

(10) Patent No.: US 11,058,460 B2
(45) Date of Patent: Jul. 13, 2021

(54) DEVICE FOR CONTROLLED PUNCTURING OF AN OBJECT

(71) Applicants: Mohamed Zanaty, Neuchâtel (CH); Charles Baur, Saint-Aubin (CH); Simon Henein, Neuchâtel (CH)

(72) Inventors: Mohamed Zanaty, Neuchâtel (CH); Charles Baur, Saint-Aubin (CH); Simon Henein, Neuchâtel (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 360 days.

(21) Appl. No.: 16/315,974

(22) PCT Filed: Jul. 20, 2017

(86) PCT No.: PCT/EP2017/068344
§ 371 (c)(1),
(2) Date: Jan. 7, 2019

(87) PCT Pub. No.: WO2018/015488
PCT Pub. Date: Jan. 25, 2018

(65) Prior Publication Data
US 2020/0222080 A1    Jul. 16, 2020

(30) Foreign Application Priority Data

Jul. 20, 2016 (EP) .................................. 16180443
Sep. 21, 2016 (EP) .................................. 16190005

(51) Int. Cl.
*A61B 17/34* (2006.01)
*A61B 34/30* (2016.01)
(Continued)

(52) U.S. Cl.
CPC .......... *A61B 17/3496* (2013.01); *A61B 34/30* (2016.02); *A61M 5/20* (2013.01);
(Continued)

(58) Field of Classification Search
CPC .......... A61B 2090/064; A61B 17/3496; A61B 34/30; A61B 2090/034; A61B 2090/033;
(Continued)

(56) References Cited

U.S. PATENT DOCUMENTS 5,320,610 A    6/1994  Yoon
5,336,176 A    8/1994  Yoon
(Continued)

FOREIGN PATENT DOCUMENTS

WO    00/09184 A1       2/2000
WO    2013/029039 A1    2/2013
WO    2015196085 A2     12/2015

OTHER PUBLICATIONS

International Search Report dated Oct. 27, 2017, issued in corresponding International Application No. PCT/EP2017/068344, filed Jul. 20, 2017, 4 pages.
(Continued)

*Primary Examiner* — Wade Miles
(74) *Attorney, Agent, or Firm* — Christensen O'Connor Johnson Kindness PLLC

(57) ABSTRACT

The present invention relates to a A device for puncturing an object, in particular a bodily vein, comprising: a body defining an inner cavity with at least one opening and a perforating needle extending in the cavity and being movable in the cavity between a resting position and an active position where the needle extends at least partially through the opening outside the cavity, and actuating means arranged to move the needle between the resting and active positions. The actuating means comprises a tuneable multistable driv-
(Continued)

ing mechanism comprising at least a multistable element having a determined switching load, the multistable element being fixedly arranged between the needle and an inner wall of the cavity, and an actuator for transmitting energy to move the needle between the resting and active positions when the energy reaches the switching load.

23 Claims, 5 Drawing Sheets

(51) Int. Cl.
*A61M 5/20* (2006.01)
*A61M 5/32* (2006.01)
*A61B 90/00* (2016.01)
*A61B 17/00* (2006.01)
*A61F 9/00* (2006.01)
*A61F 9/007* (2006.01)

(52) U.S. Cl.
CPC ........ *A61M 5/3293* (2013.01); *A61M 5/3295* (2013.01); *A61B 2017/00407* (2013.01); *A61B 2090/034* (2016.02); *A61B 2090/064* (2016.02); *A61B 2217/007* (2013.01); *A61F 9/007* (2013.01); *A61F 9/0008* (2013.01); *A61M 2205/332* (2013.01); *A61M 2205/587* (2013.01)

(58) Field of Classification Search
CPC ....... A61B 5/150374; A61B 5/150534; A61M 2205/332; A61F 9/007
See application file for complete search history.

(56) References Cited

U.S. PATENT DOCUMENTS

| | | |
|---|---|---|
| 8,419,764 B2 | 4/2013 | Begg |
| 8,894,679 B2 | 11/2014 | Begg |
| 2008/0039789 A1 | 2/2008 | Wyrick |
| 2014/0239600 A1 | 8/2014 | Walsh et al. |

OTHER PUBLICATIONS

Written Opinion of the International Searching Authority dated Oct. 27, 2017, issued in corresponding International Application No. PCT/EP2017/068344, filed Jul. 20, 2017, 5 pages.

De Smet, M.D., et al., "Robotic Assisted Cannulation of Occluded Retinal Veins," PloS one 11(9):e0162037, Sep. 2016, 16 pages.

Gonenc, B., et al., "Robot-Assisted Retinal Vein Cannulation with Force-Based Puncture Detection: Micron vs. the Steady-Hand Eye Robot," 2016 IEEE 38th Annual International Conference, IEEE, pp. 5107-5111, Aug. 2016.

DEVICE FOR CONTROLLED PUNCTURING OF AN OBJECT

TECHNICAL FIELD

The present invention relates to the field of medical devices and in particular to a puncturing device for safely and repeatably puncturing an object, in particular a bodily vein such as a retina vein, with a controlled and repeatable stroke independently from the manual actuating force of a practitioner.

PRIOR ART

Treatment of retinal vein occlusion requires retinal vein cannulation through puncturing for drug delivery onsite within the retinal vein in order to reduce blood clots and avoid vision loss of a mammal patient.

The force needed for the cannulation is just at the limit of the surgeon touch sensing capabilities (i.e. 10 mN). Therefore, the surgeon will not feel in his hand the occurrence of the cannulation process. During the cannulation a serious risk of non-puncturing exist, which can lead to harmful bleedings and/or incorrect injection of the drug.

Currently, dedicated robots are used for the control of the cannulation as discussed in A. Gijbels et al., IEEE conf. Robotics and Automation, Washington, May 2015 or A. Uneri et al, Int. Conf. On Biomedical Robotics, Japan, September 2010. These robots are bulky and expensive. Handheld device were also introduced based on compliant mechanism for the puncturing process.

A self-retracting tool was developed for laparoscopic surgery was also proposed in U.S. Pat. No. 8,894,679. The tool consists of a preloaded spring that retracts the tool head when there is a drop in force during puncturing. The tool has only one stable position and requires additional equipment for drug delivery. Besides, no force feedback is provided to the surgeon during the puncturing forces, which implies that the surgeon can not precisely control the puncture process.

Another self-retracting tool was proposed in U.S. Patent Application No. US 20140239600 A1. The tool consists of drill mounted on a bistable mechanism. When there is a sudden drop in puncturing force, the drill retracts as the bistable mechanism switches. However, such drilling system is not scaled nor easily adapted for vein cannulation, as such require much more care and precision in stroke application.

A cannulation device has been proposed in PCT application WO-2015196085-A2. The tool is designed to limit the perforation depth of the needle inside the vein with stoppers. However, the tool does not limit the force imposed by the surgeon. This can lead to serious complications in the case of incorrect positioning of the tool. Moreover, it has only one stable position and therefore the surgeon has to maintain application of a force on the tool to keep the needle in position inside the vein, which is difficult to control. Importantly, no force feedback is provided to the surgeon.

A new compliant needle for retinal vein cannulation was also recently presented in B. Gonenc, N. Tran, P. Gehlbach, R. H. Taylor, and I. lordachita, Robot-assisted retinal vein cannulation with force-based puncture detection: Micron vs. the steady-hand eye robot," in Engineering in Medicine and Biology Society (EMBC), 2016 IEEE 38th Annual International Conference of the, pp. 5107{5111, IEEE, 2016. According to that paper, the needle can be used with a handheld device or robotic system and is controlled by actuators for precise control, and it has an Fiber Bragg Grating strain sensors held on its tip for detecting the puncture process.

Another solution was proposed in M. D. de Smet, T. C. Meenink, T. Janssens, V. Vanheukelom, G. J.Naus, M. J. Beelen, C. Meers, B. Jonckx, and J.-M. Stassen, Robotic assisted cannulation of occluded retinal veins," PloS one, vol. 11, no. 9, p. e0162037, 2016. In this submission a trocar is held on a robot to precisely control the cannulation.

These solutions are unfortunately complicated and require active control. There's therefore a need for a simple, repeatable, accurate and preferably light solution for performing cannulation of bodily vessels and veins.

DISCLOSURE OF THE INVENTION

The present invention aims at providing an improved puncturing device for safely and repeatably puncturing an object such as a bodily vein of a patient for example, and in particular a retina vein, which is not suffering the defaults or disadvantages of the automated and robotized devices of the prior art.

In particular, the present invention aims at providing a puncturing device which can be used manually by practitioner such as a surgeon to safely puncture a retina vein of a patient without risking over-perforating the vein under the manual stroke of the surgeon.

The invention achieves its aims by providing a puncturing device according to claim 1. The proposed inventive device is safe and well controlled based on the use of force driven multistable mechanisms, as defined hereafter.

Preferable features of the device of the invention are also recited in the dependent claims.

The puncturing device of the invention advantageously comprises:
- a body defining an inner cavity with at least one opening and
- a perforating needle extending in said cavity and being movable in said cavity between a resting position and an active position where the needle extends at least partially through said opening outside said cavity, and
- actuating means arranged to move said needle between the resting and active positions.

The puncturing device of the invention is further characterized in that the actuating means comprises a tuneable multistable driving mechanism comprising at least a multistable element having a determined switching load, said multistable element being fixedly arranged between said needle and an inner wall of the cavity, and an actuator for transmitting energy to move the needle between said resting and active positions when said energy reaches said switching energy.

Compared to the previous puncturing tools of the prior art the device of the invention provides a controlled force and displacement of the needle imparted by the multistable driving mechanism actuated through the actuator, controlled either by a surgeon or a robot for example. Moreover, the resting and active positions correspond to at least two stable positions of the needle, enabling for a surgeon to maintain a stable position inside the vein without efforts thanks to the multistable, for instance bistable driving mechanism.

In addition, according to preferable configurations of the device of the invention as defined in the dependent claims the device of the invention has a tuneable stroke thanks to abutment means that help controlling the course of the needle to just the right distance inside the vein.

In addition, force feedback measurement can be easily implemented either optically or mechanically by adding force sensors on the tip of the tool and/or, in preferable embodiments by producing the device in glass or fused silica.

In embodiments of the invention, the multistable driving mechanism is a bistable driving mechanism configured for translating said needle along a direction normal to a surface of the object to be punctured.

In embodiments of the invention, the multistable driving mechanism is a rotational bistable driving mechanism driving said needle about a curved trajectory.

In embodiments of the invention, the needle is mounted on a needle holder arranged in the cavity to cooperate with the tuneable multistable driving mechanism at least.

In embodiments of the invention, the puncturing device further comprises springs arranged between said actuator and said needle holder or between said needle holder said cavity inner wall, the maximum imposed force of said springs being higher than the switching load.

In embodiments of the invention, the switching load is tuneable. In particular, said body may be flexible to vary a compressive load applied from the inner wall of the cavity on said multistable element.

In embodiments of the invention, the distance between said resting position and said active position of the needle is tuneable.

In embodiments of the invention, it further comprises abutment means arranged in said cavity to limit the course of the needle or needle holder and adjust the distance between said resting and active positions.

Preferably, the abutment means comprises a flange or ridges extending in said cavity to engage with part of the needle or needle holder when it reaches said active position.

Alternatively, the abutment means may comprise a ratchet mechanism comprising notches and ridges arranged on the inner wall of said cavity and the needle or needle holder respectively so as to provide a stepped displacement of the needle between its resting and active positions.

In embodiments of the invention, the device further comprises a guard secured or arranged about the opening of the cavity of the body to provide a reference position of the needle with respect to a surface of the object to be punctured.

In embodiments of the invention, the multistable element comprises buckled beams, preferably pre-shaped buckled beams, or a buckled membrane.

Alternatively the multistable element comprises folded beams.

In embodiments of the invention, the actuator comprises a piston movable in said cavity of the body along a longitudinal axis thereof or a rotating hub rotatable about a centre of rotation. Said actuator may further comprise a handle for manual or robotized control thereof.

Preferably, said needle and/or said needle holder comprises a microfluidic channel extending therein.

In embodiments of the invention, said needle may also comprise multiple puncturing tips flexibly mounted about articulations with respect to a head of the needle.

In embodiments of the invention, said body, said multistable driving mechanism and said needle are made of any of the following materials: titanium alloys, stainless steel, glass or silicon. In embodiments of the invention, they are made of a monolithic piece of material.

Finally, the device of the invention may also comprise force sensors at the tip of the needle to provide a force feedback or such a force feedback can also be obtained through optical properties.

PRESENTATION OF DRAWINGS

The invention will be better understood in view of the following description of detailed embodiments thereof in reference to the drawings wherein.

DESCRIPTION OF PREFERRED EMBODIMENTS

The present invention relates to an improved puncturing device 1, which can be used in particular, but not exclusively, for the eye surgery and in particular for retinal vein cannulation.

Figure 1:
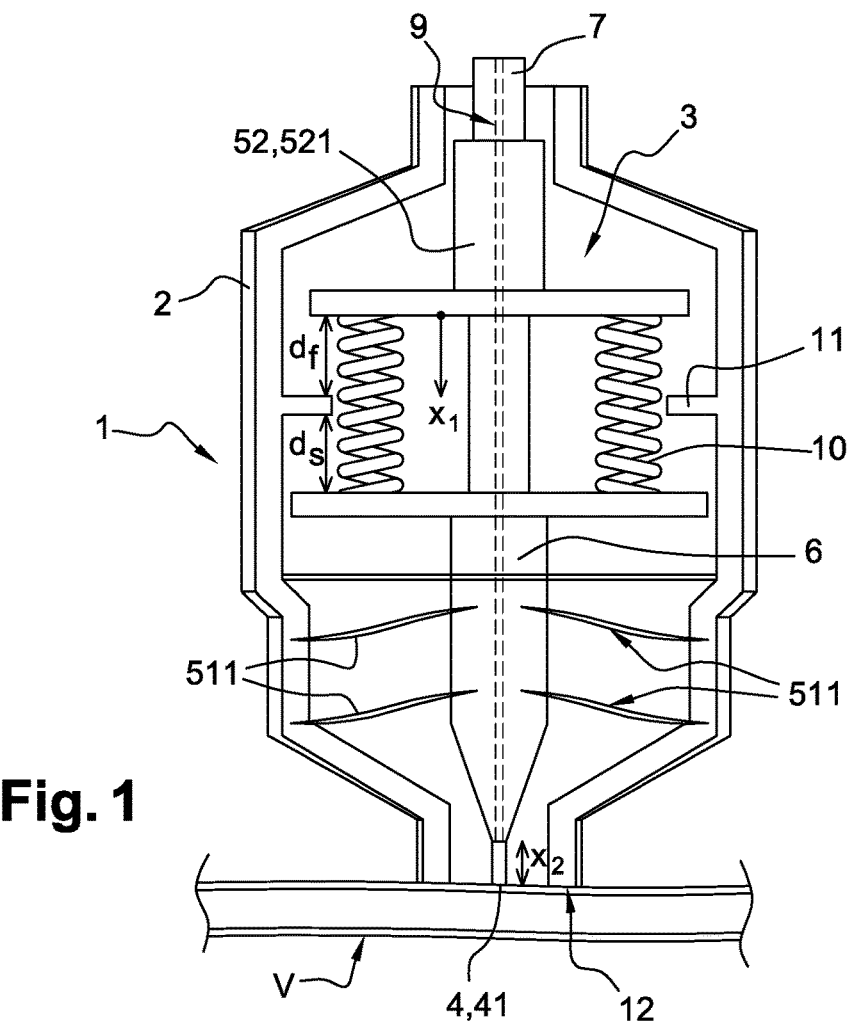
FIG. 1 represents a cut-of view of a first embodiment of a 3D puncturing device of the invention showing a linear bistable actuation mechanism of the puncturing needle.

A first embodiment of such puncturing device 1 is represented schematically in FIG. 1. The puncturing device 1 is mainly used for the precise control of the stroke of a puncturing needle 4 with respect to the surface of the tissue to be punctured. i.e. a retinal vein V. This ensures that the needle 4 reaches the lumen of the vein V, thus to ensure its cannulation for drug delivery.

The main advantage of the device 1 of the invention is that the stroke of the device is predefined independently of the displacement exerted by an operator, i.e. a surgeon or a robotized puncturing system. In addition, the puncturing device 1 of the present invention is low cost, safe and easy to use.

FIG. 1 shows a cut-off view of a first embodiment of a puncturing device 1 according to the invention, wherein a bistable driving mechanism 51 with a predefined force and displacement values for a puncturing needle 4 is proposed.

The puncturing device 1 comprises an outer body 2 defining an inner cavity 3 wherein a needle 4, comprising a needle holder 6 supporting said needle 4 is arranged. The needle 4 and its holder are movable between a resting position, where the needle 4 is fully retracted inside the cavity 3, and an active position where the needle extends outside the cavity to perforate a vein V where a drug needs delivering. The displacement between the said resting and active positions of the needle 4 is controlled and driven by actuating means 5 comprising a multistable, in particular a bistable, driving mechanism 51 and an actuator 52 to impart an actuation load on the bistable driving mechanism 51.

The needle holder 6 is connected to the inner wall of the cavity 3 by means of said bistable driving mechanism 51. Further a cylinder 7 is connected to the needle holder 6 through a piston 521 forming part of the actuator 52, said piston 521 being slidably mounted in the cavity 3. The piston 521 preferably comprises, over the cylinder 7, a handle 522 (visible in FIG. 2) extending outwardly from the body 2 for manual or robotized control and actuation of the actuator and driving mechanism 51. A fluidic channel 9 is advantageously integrated inside the cylinder 7, needle holder 6 and extending towards the needle 4 for drug delivery in the vein V to be punctured.

When an operator of the device, i.e. a surgeon or robot, imparts a force on the handle 522, the piston 521 undergoes a displacement $x_1$ with respect to the body 2. The piston 521 is connected to the needle holder 6 by elastic means, such as helical compression springs 10 or a folded beam arrangement. Thus, the displacement $x_1$ of the piston 521 imposes force on the needle holder 6, which translates the needle 4 from its resting position towards the active, perforating, position in the vein V.

The bistable driving mechanism 51 comprises axially or pre-shaped buckled beams 511, which provide both a bearing function for the needle holder 6 and a tuneable bistable stiffness behaviour. The number and/or geometry of the buckled beams 511 and their orientation with respect to the needle holder 6 on the one hand and cavity's inner wall on the other hand can advantageously be chosen and designed depending on the switching load one wants to set for the bistable driving mechanism 51 of the needle 4.

In particular, the shape of the buckled beams 511 is properly designed to show tuneable bistability response through modifying the axial preload. For tuning the force and stroke of the needle 4, an external O-ring spring can be used for imposing radial compression forces on the body's outer wall and thereby the buckled beams 511 of the multistable driving mechanism 51 arranged in the cavity 3 inside the body 2. Based on the stiffness of the external compression ring, the switching load of the buckling beams 511 can be modified.

Abutment means such as stoppers 11 are further preferably used to limit the displacement of the needle holder 6 to a precise value $d_s$ with respect to the body 2, independent of an actuation force on the actuator 52, from a surgeon or robot gesture $x_1$. The distance $d_s$ can be tuned manually by the operator before or during the operation.

With the previously described configuration, the puncturing device 1 of the invention is such that the maximum force $F_{max}$ that can be imparted to the actuator 52 depends on the stiffness of the springs 10 and the distance to the stopper 11 given as $d_f$. Importantly, the switching load of the bistable mechanism 51 must be less than $F_{max}$.

Therefore the design of the puncturing device 1 of the invention is based on using a bistable mechanism 51 with a predefined force and displacement values.

The body 2 may be further equipped with a guard 12 near the bottom end thereof, about the needle's tip 41. This guard 12 is arranged to be pressed by the device operator, such as a surgeon, against the vein V to be punctured, thus making the reference of the $x_2$ displacement of the needle's tip 41 beyond the guard 12 to perforate the vein V coincide precisely with the surface of the tissue. This ensures that the needle's tip 41 will move by the distance $x_2$ in the lumen below the surface of the vein V. The shape of the guard 12 can be designed with a groove that provides an additional stabilizing effect to the vein V, thus reducing the risk of lateral movement of the vein V during puncture. The needle's tip 41 is used for the puncturing of the vein V and delivery of drug into the lumen of said vein V.

As an alternative to the construction of the device shown in FIG. 1 where the bistable mechanism 51 comprises buckled beams 511, a buckled membrane (not represented) may be used instead of the buckled beams 511 to increase the energy released by the device per unit volume.

Figure 2:
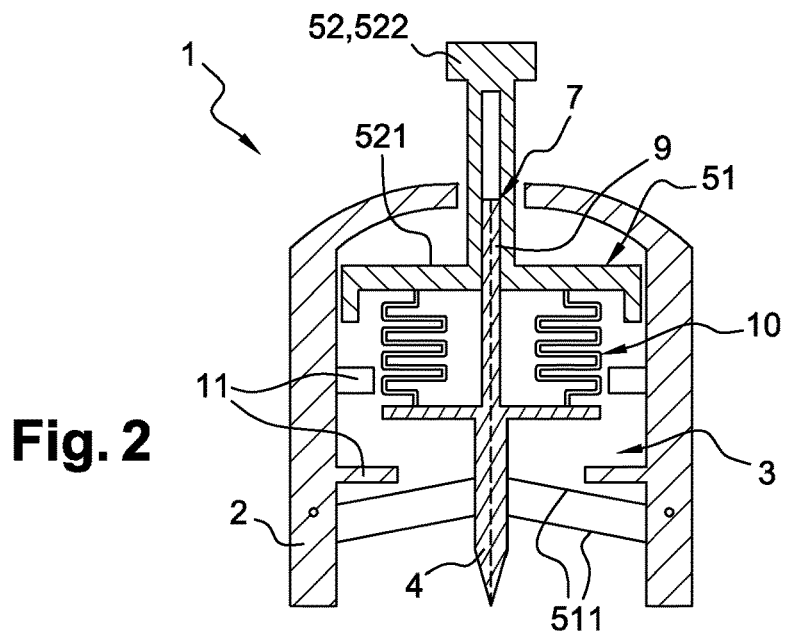
FIG. 2 represents a 2D variant of the puncturing device of FIG. 1.

The puncturing device 1 of the invention can be adapted with 2D manufacturing techniques, such as with etching techniques of silicon for instance, to obtain a puncturing device 1 as represented by the embodiment of FIG. 2. In that embodiment springs 10 are formed as compressible serpentine springs to control the applied force. As for the embodiment of FIG. 1, an axial load can be provided by means of an external compression means to control the applied force by the bistable mechanism 51 and its buckled beams 511.

Figure 3A:
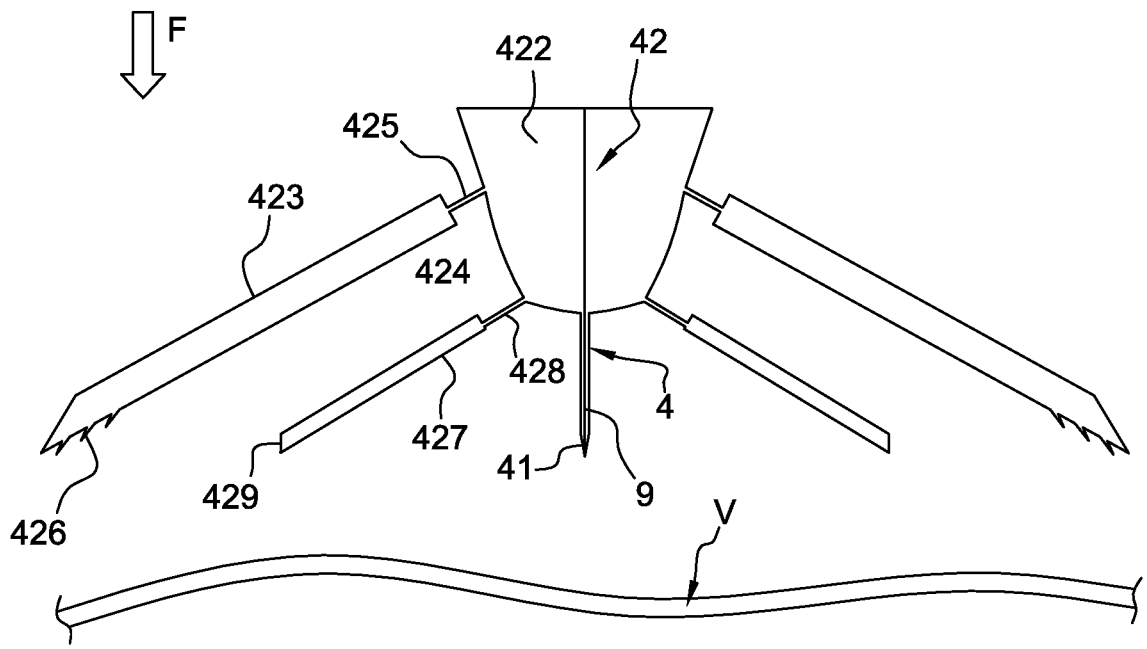
FIGS. 3A and 3B and 3C represent alternative needle heads for a puncturing device according to the invention.

A regular issue encountered during cannulation operations of the vein V in normal directions to the outer surface thereof is the increased risk of the movement of the vein due to its elasticity, therefore, the wrong injection of the drug outside the vein. To solve such problem, a translational puncturing head 42 bearing a puncturing needle 4 is shown in FIG. 3A. This puncturing head design comprises a body 422 from which extends at a bottom end a puncturing needle 4 having a microfluidic channel 9 extending there through to deliver a drug or solution at the punctured site. The puncturing head 42 further comprises a pair of anchoring legs 423 and a pair of stretching legs 424 that help to improve the puncture process efficiency. Anchoring legs 423 extend laterally and symmetrically to the head's body 422 and are articulated thereon about compliant joints formed of flexible blades 425. The anchoring legs 423 consists of linearly extending members comprising at a free end opposite a compliant joint 425 segregated teeth 426. The teeth 426 help preventing the anchoring legs 423 from slippage upon pressing on the tissue to be punctured or one nearby, thereby providing a stable resting point for the puncturing head 42. Next to the anchoring legs 423 are provided stretching legs 424, each formed of a rigid longitudinal member 427 connected at an end to the head's body 422 about a flexible compliant joint made of a flexible blade 428 and, opposite the blade 428 a stretching edge 429.

Variations of designs of the puncturing head 42 show in FIG. 3A are possible, for instance where only the puncturing needle 4 and anchoring legs 423 or puncturing needle and stretching legs 424 are used.

Figure 7:
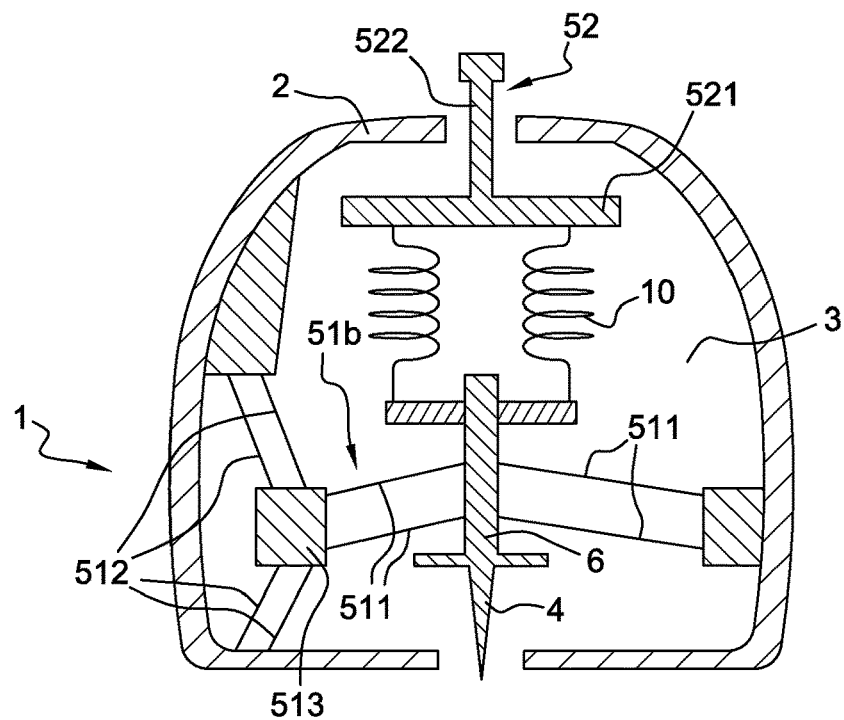
FIG. 7 represents a fourth embodiment of a puncturing device of the invention showing a tristable actuation mechanism of the puncturing needle.

The puncturing needle 4 of the puncturing head 42 of FIG. 3A is used in a translational puncturing device 1 as shown in FIG. 1 or 2 or FIG. 7 as described hereinafter.

Once the multistable driving mechanism 51 is actuated by means of actuator 52, the anchoring legs 423 apply on the tissues surrounding a vein V, a cavity or any target to be punctured by the needle 4, or the zone of interest itself. The teeth 426 penetrate in the tissues on which the anchoring legs 423 apply and function as a support for the puncturing device 1, in lieu for instance of the guard 12 of FIG. 1. After that the stretching legs 424 get in contact with the vein V or any target through their stretching edges 429, which exert a stretching force onto the vein V. Finally, the puncturing needle 4 gets in contact with the vein V and perforates it under the pressing load from the multistable mechanism 51. The fluidic channel 9 then provides a path for the injection of a drug and/or solution inside the vein V or selected target.

Figure 3B:
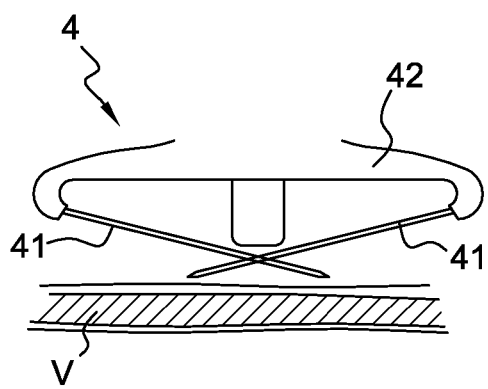
Figure 3C:
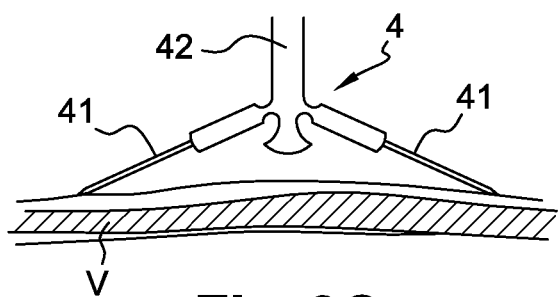

Further variants of a needle 4 are shown in FIGS. 3B and 3C, which comprise a dual-tip head 42 to avoid over puncturing. Such shapes, whereby the needles 4 are mounted to the double-tip puncturing head 42 about flexible articulations 421 allow lateral puncturing of a vein V through normal actuation of the bistable driving mechanism 51.

Figure 4:
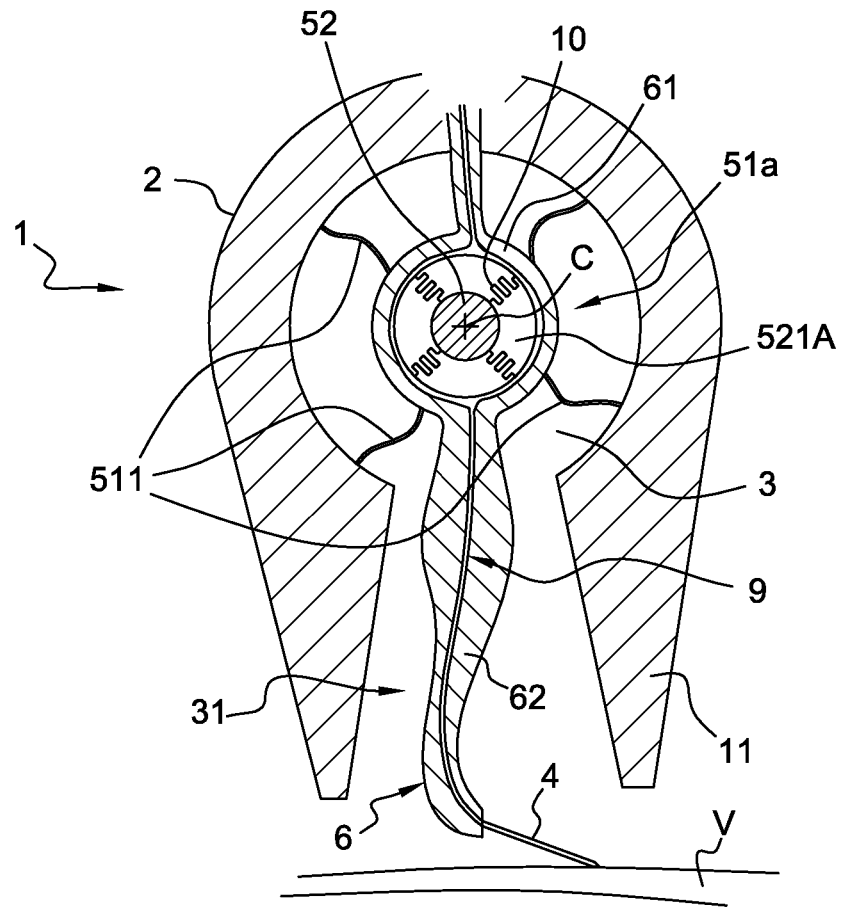
FIGS. 4, 5 and 6 represent three variants of a second embodiment of a puncturing device according to the invention showing a rotational bistable actuation mechanism of the puncturing needle leading to lateral puncturing.
Figure 5:
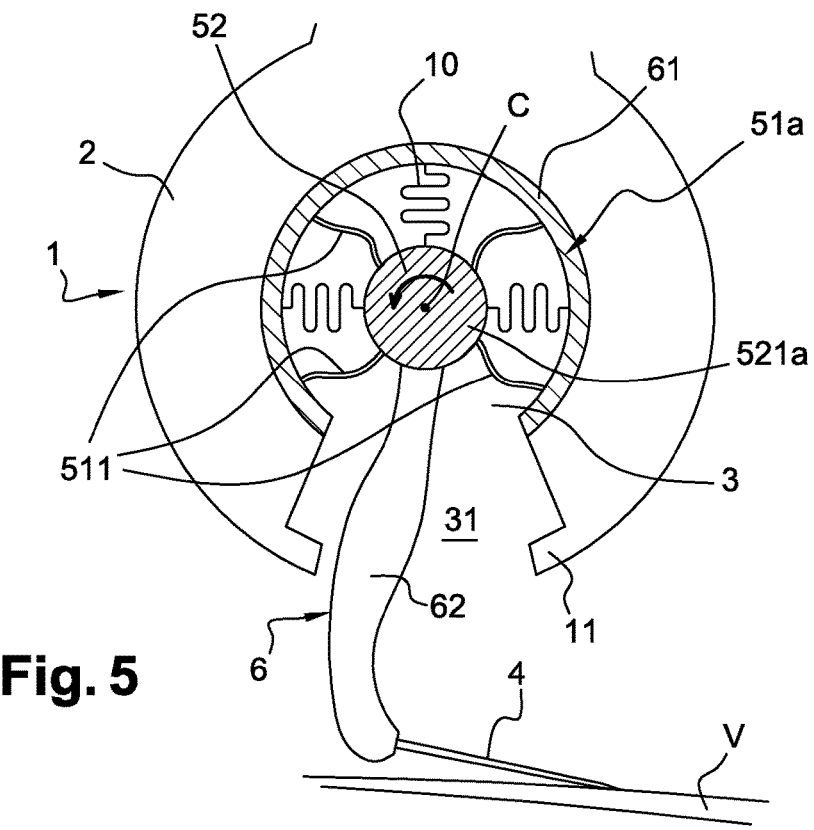
Figure 6:
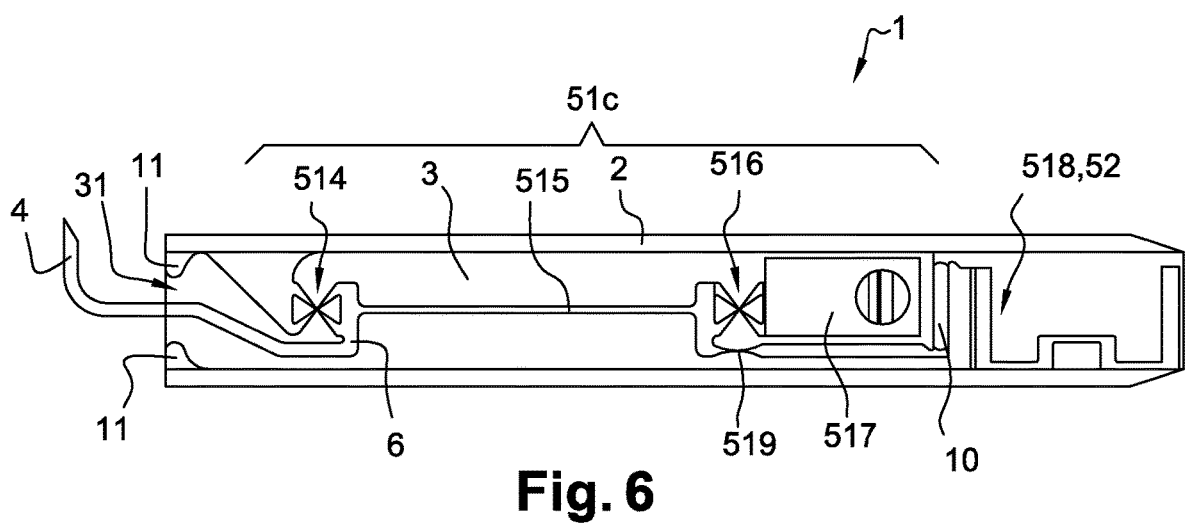

FIGS. 4, 5 and 6 further represent a second embodiment of a puncturing device 1 according to the invention. Instead of the translational bistable driving mechanism 51 of the device shown in FIGS. 1 and 2, the puncturing device 1 of FIGS. 4 and 5 relies on the provision of a rotational bistable driving mechanism 51a in the device body 2 for driving the needle holder 6 and needle 4 in a substantially rotating puncturing trajectory having a tangential component to the surface of the object to be punctured.

Such rotational bistable driving mechanism 51a therefore allows for lateral puncturing of the vein V instead of normal puncturing.

The rotational bistable driving mechanism 51a is arranged in a cavity 3 of a clamp-shaped device body 2. The body 2 comprises a cavity opening 31 configured to allow a needle holder 6 equipped with a puncturing needle 4 to move angularly within the opening 31 to allow puncturing upon actuation of the driving mechanism 51a as described below.

By angular movement of the needle holder 6 within the cavity opening 31 it must be understood that said holder 6 can move within a determined angular sector centered on a center of rotation C of the rotational driving mechanism 51a to which the needle holder 6 is attached. Hence the cavity opening 31 shows preferably a substantially conical shape in a longitudinal cross-section of the device 1 as represented in FIGS. 4 and 5. That conical shape of the cavity opening 31 is advantageously further delimited by stoppers 11 limiting the course in rotation of the needle holder 6.

The needle holder 6 is preferably formed of an arm 62 held at an end to a substantially cylindrical drum 61 and holding the puncturing needle 4 at an opposite free end of the arm 62. Said drum 61 forms a part of the bistable driving mechanism 51a by accommodating a rotating actuator 52 comprising a hub 521 inserted coaxially in the drum 61 and movable in rotation about the center of rotation C within said drum. Further rotational springs 10a extend between an outer surface of the hub 521 and an inner surface of the drum 61 or, as shown in FIG. 5, extending between an outer surface of the drum 61 and an inner surface of the cavity 3.

In addition, buckled beams 511 extend between the outer surface of the drum 61 and an inner surface of the cavity 3 arranged in a device body 2. A handle (not represented) may finally be provided to allow manual or automatized action on the actuator 52 to make it turn about the center C to load the bistable driving mechanism 51a until the switching load thereof is reached, when the drum 61 then rotates under the driving force liberated by the buckled beams 511 to perform a stroke of the needle 4.

As previously introduced, the stoppers 11 are arranged in the body 2 to avoid over puncturing effect of the needle 4 upon rotation of the drum 61 of needle holder 6.

Again, a microfluidic channel 9 is foreseen in the needle holder 6 to allow delivering a drug with the needle 4.

Also, an external elastic O-ring can be used to tune the switching load of the bistable driving mechanism 51a, for instance by compressing said ring about the outer surface of the body 2, which may be flexible about its cavity opening 31.

FIG. 6 shows a puncturing device 1 according to a fourth embodiment of the invention. In this embodiment the puncturing device 1 comprises a needle 4 arranged movably within and out of a cavity 3 defined in a substantially tubular body 2 by means of an a bistable mechanism 51c comprising a first flexural pivot 514 connected to one extremity of a transmission beam 515 comprising an internal microfluidic channel 9 and to which the needle 4 is attached, the needle 4 being in fluidic communication with the microfluidic channel 9 in the beam 515. The other extremity of the transmission beam 515 is connected to a second flexural pivot 516, which is in turn connected on a tuning stage 517, attached to the body 2 inner wall by two parallel flexible beams (not represented). Second flexural pivot 516 is configured to be actuated by an actuator 52 comprising an actuation stage 518 and an actuation spring 10 and a compliant joint 519 formed of a thin flexible blade.

The device 1 of FIG. 7 can be manually or machine-operated as following. The bistable driving mechanism 51c is arranged for delivering a constant amount of energy for retinal vein cannulation independent of the applied force on the actuation stage 518 by an operator. A displacement is applied to the tuning stage 517 to preload the beam 515 such that it works as a bistable mechanism. Actuation stage 518 switches the bistable mechanism 51c between its stable states. The range of motion of the needle 4 in rotation about pivot 514 is limited by the body 2, in particular by stoppers 11 arranged about the cavity opening 31.

Compared to other designs, design in FIG. 6 can easily fit in the required space constrain for the eye surgery. Besides, the bistable mechanism being a pinned-pinned beam, it shows an instantaneous snapping of the needle tip.

FIG. 7 represents a further embodiment of a puncturing device 1 of the invention comprising a multistable, for instance tristable, driving mechanism 51b for driving a puncturing needle 4 and/or the needle holder 6 in a translational, normal stroke towards a tissue to be punctured.

In this embodiment the puncturing device 1 is very similar to that of FIGS. 1 and 2 except for secondary pairs of buckled beams 511' arranged substantially vertically in a lateral recess 21 in an inner wall of the body 2 of the device and being connected at their ends to the recess wall on the one hand and to a beams node 53 on the other hand, said beams node 513 further being connected to a primary pair of buckled beams 511 in direct connection to the needle holder 6.

This configuration of a puncturing device 1 is particularly advantageous in that it allows for several stable puncturing positions for the needle 4 inside or outside a vein V, thanks to a staged translational movement of the needle holder 6 upon actuation through the handle 522 of the actuator 52. Indeed, in a first stage the needle holder 6 moves a first step when the switching load of the primary pairs of buckled beams 511 is reached. Then if an operator continues to apply force onto the actuator 52 it may continue with a second step when the switching load of the secondary pairs of buckled beams 511' is reached, causing beams node 53 to be pressed in the recess 21 and the needle 4 thereby going deeper into a perforated tissue.

As for the devices of FIGS. 1 and 2, the switching load of the tristable driving mechanism 51b can be adjusted by axial compression forces applied, for instance with a ring, on the outer walls of the device body 2. In this embodiment, the body 2, the actuator 52 structure and springs 10 are similar to those of FIGS. 1 and 2 and do not need further description.

Figure 8A:
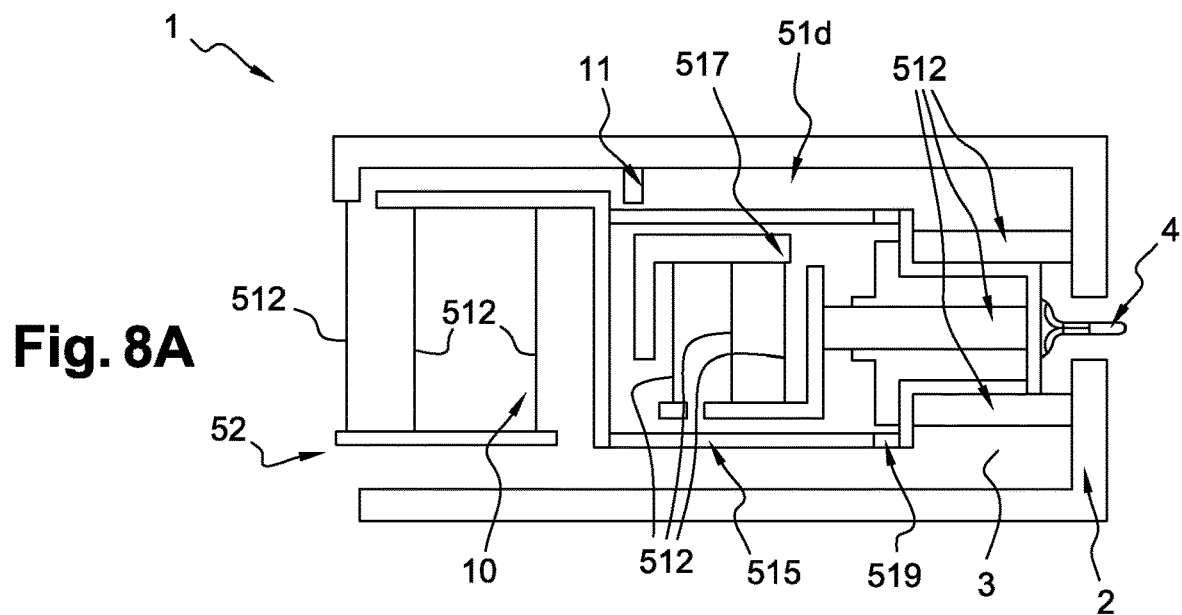
FIGS. 8A and 8B represent a fifth embodiment of a puncturing device of the invention showing an out of plane multistable actuation mechanism of the puncturing needle.
Figure 8B:
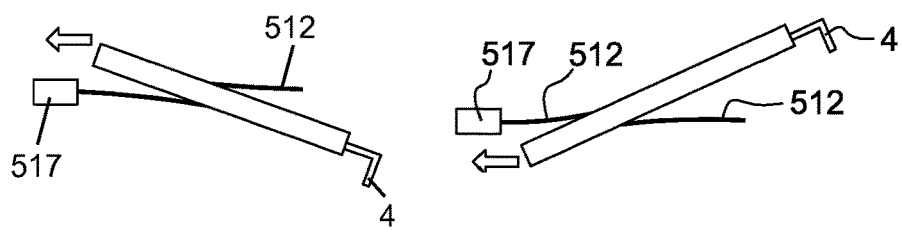

FIGS. 8A and 8B show a further embodiment of a puncturing device according to the principles of the present invention, relying on the use of out of plane folded beams in lieu of buckled beams 511, 511' as provided in the previous embodiments. Folded beams mechanisms are tension based bistable mechanisms and have the advantage of being long stroke low force mechanisms which are more convenient for retinal vein occlusion procedure. On the kinematic side, folded beam mechanisms have an out of plane motion. The actuator and the needle move in two orthogonal planes.

A fifth embodiment of the puncturing device 1 of the present invention is presented in FIGS. 8A and 8B, respectively in a top view and side view of the puncturing device 1. In this configuration, the puncturing device 1 comprises a bistable, out-of-plane, driving mechanism 51d for a puncturing needle 4. The bistable mechanism 51d comprises folded beams 512 extending between the walls of a U-shaped body frame 2 and out of plane rods 515 and compliant joints 519. Out of plane rods 515 are connected to an actuation spring 10 formed of folded beams 512 which is connected to body frame 2. An abutment ridge 11 limits the range of motion of the actuation spring 10.

The bistable mechanism 51d of the device 1 of FIG. 8 is based on out of plane folded beam mechanism. A tuning stage 517 with a transverse displacement, is arranged in a cavity 3 between the body frame walls to impart a tension load on folded beams 512 for the mechanism 51d to become an out of plane bistable mechanism. The actuation of the mechanism is done through applying a displacement on the actuation spring 10 which in turns leads to a force which drives folded beams 512 bearing the out of plan rods 515. As the value of the preload of the tuning stage changes, the force at the needle tip 41 changes as well.

The device of the present invention has been described hereinbefore in the context of an application to the puncturing of a retinal vein but it can be used for many other applications in the medical in general, in particular in surgery, radiology or general patient's care.

Indeed, the puncturing device 1 of the invention provides safe and controlled puncturing which can be helpful in the field on interventional radiology, where the capability of the device to penetrate and lock one or multiple needle into a target is key issue.

The device of the invention can also be used for to collect and/or interact with bodily fluids (e.g. cerebrospinal fluid) and provide a more efficient alternative to existing solution. Drug delivery performed by caregivers or by patients themselves can also be extended using the device of the invention.

In must also be noted that the principles of for controlling stroke and force used in the device of the invention could also be used on several surgical tools. For example, to cut tissues in a controlled manner can extend existing surgical cutters (e.g. microsurgery).

Overall, the device of the invention and its working principles may be used is the following non exhaustive list of puncture related medical operations:

Abdominal access in laparoscopic surgery.
Epidural anesthesia,
Thoracentesis,
Cranial perforations,
Blood drawings,
Joint access in arthroscopic surgery,
Spinal taps,
Tube Thoracostomy,
Abscess drainage,
Cricothyrotomy surgery,
Tracheostomy surgery,
Hemodialysis access,
Amniocentesis,
Cardiac catheters,
PICC Line placement,
Punch biopsy,
Thoracoscopy,
Fine needle aspiration,
Hemodialysis,
Diabetes blood sample collection,
Intra-veinal drug injection by non-professional,
Hair implant.

It is finally important to underline that the technical principle of the device of the invention can also be used in non-medical fields (e.g. Industrial field), such as for example:

Quality control of products based on elastic materials (e.g. inkjet printed sensors),
Puncturing process performed close to high pressure chambers (sensitive areas),
Puncturing of a stack of materials,
Material identification,
Intra-layer fluid injection and drawing,
Puncture of cells to collect/inject substances (biology),
Leather manufacturing,
Piercing industry.

The invention claimed is:

1. A device for puncturing an object, comprising:
a body defining an inner cavity with at least one opening;
a perforating needle extending in said cavity and being movable in said cavity between a resting position and an active position where the needle extends at least partially through said opening outside said cavity; and
actuating means arranged to move said needle between the resting and active positions,
wherein the actuating means comprises a tuneable multistable driving mechanism comprising at least a multistable element having a determined switching load, said multistable element being fixedly arranged between said needle and an inner wall of the cavity, and an actuator configured for transmitting energy to move the needle between said resting and active positions when said energy reaches said switching load.

2. The device according to claim 1, wherein the multistable driving mechanism is a bistable driving mechanism configured for translating said needle along a direction normal to a surface of the object to be punctured.

3. The device according to claim 1, wherein the multistable driving mechanism is a rotational bistable driving mechanism driving said needle about a curved trajectory.

4. The device according to claim 1, wherein the needle is mounted on a needle holder arranged in the cavity to cooperate with at least the tuneable multistable driving mechanism.

5. The device according to claim 4, further comprising springs arranged between said actuator and said needle holder or between said needle holder and said cavity inner wall, the maximum reaction force of said springs being higher than the switching load.

6. The device according to claim 1, wherein the switching load is tuneable.

7. The device according to claim 6, wherein said body is flexible to vary a compressive load applied from the inner wall of the cavity on said multistable element.

8. The device according to claim 1, wherein the distance between said resting position and said active position of the needle is tuneable.

9. The device according to claim 8, further comprising abutment means arranged in said cavity to limit the course of the needle or needle holder and adjust the distance between said resting and active positions.

10. The device according to claim 9, wherein the abutment means comprises a flange or ridges extending in said cavity to engage with part of the needle or needle holder when it reaches said active position.

11. The device according to claim 1, further comprising a guard secured about the opening of the cavity of the body to provide a reference position of the needle with respect to a surface of the object to be punctured.

12. The device according to claim 1, wherein the multistable element comprises buckled beams.

13. The device according to claim 12, wherein the buckled beams are pre-shaped buckled beams.

14. The device according to claim 1, wherein the multi-stable element comprises folded beams.

15. The device according to claim 1, wherein the multi-stable element comprises a buckled membrane.

16. The device according claim 1, wherein the actuator comprises a piston movable in said cavity of the body along a longitudinal axis thereof or a rotating hub rotatable about a center of rotation.

17. The device according to claim 16, wherein said actuator further comprises a handle for manual or robotized control of said actuator.

18. The device according to claim 1, wherein said needle and/or said needle holder comprises one or more microfluidic channel(s) extending therein.

19. The device according to claim 18, wherein the device provides a force feedback to an operator through optical properties.

20. The device according to claim 1, wherein said needle comprises multiple puncturing tips flexibly mounted about articulations with respect to a head of the needle.

21. The device according to claim 1, wherein said body, said multistable driving mechanism and said needle are made of any of a material selected from a group consisting of titanium alloys, stainless steel, glass and silicon.

22. The device according to claim 1, wherein the device is made of a monolithic piece of material.

23. The device according to claim 1, further comprising force sensors at the tip of the needle to provide a force feedback.

* * * * *

UNITED STATES PATENT AND TRADEMARK OFFICE
CERTIFICATE OF CORRECTION

PATENT NO. : 11,058,460 B2
APPLICATION NO. : 16/315974
DATED : July 13, 2021
INVENTOR(S) : M. Zanaty et al.

Page 1 of 1

It is certified that error appears in the above-identified patent and that said Letters Patent is hereby corrected as shown below:

On the Title Page

| Column | Line | |
|---|---|---|
| Item (73) Abstract | 1 | change "The present invention relates to a A device" to -- A device --. |

In the Claims

| Column | Line | |
|---|---|---|
| 11 | 23 | change "of any of a" to -- of a --. |

Signed and Sealed this
Thirty-first Day of May, 2022

Katherine Kelly Vidal
*Director of the United States Patent and Trademark Office*